United States Patent [19]
Webb

[11] Patent Number: 5,948,953
[45] Date of Patent: *Sep. 7, 1999

[54] POSITIONAL CLONING OF BROWN STEM ROT RESISTANCE GENES IN SOYBEANS

[75] Inventor: David M. Webb, Johnston, Iowa

[73] Assignee: Pioneer Hi-Bred International, Inc., Des Moines, Iowa

[*] Notice: This patent is subject to a terminal disclaimer.

[21] Appl. No.: 08/876,103

[22] Filed: Jun. 13, 1997

Related U.S. Application Data

[63] Continuation-in-part of application No. 08/534,091, Sep. 26, 1995, Pat. No. 5,689,035.
[51] Int. Cl.$^6$ .............................. A01H 1/04; A01H 5/00; G01N 21/76; C12N 15/29
[52] U.S. Cl. .................... 800/260; 800/267; 800/265; 800/301; 800/312; 435/6; 536/23.6; 536/24.3
[58] Field of Search ..................... 800/200, 205, 800/255, DIG. 26, 265, 267, 312, 301, 298, 260; 47/58, DIG. 1; 435/6; 536/23.6, 24.3

[56] References Cited

U.S. PATENT DOCUMENTS 5,689,035  11/1997  Webb .......................... 800/200

OTHER PUBLICATIONS

Gray et al. Reaction of Mung Bean Plants to Infection by Isolates of *Phialophora gregata*. Plant Disease. vol. 78, pp. 782–785, 1994.

Willmot et al. Genetic Analysis of Brown Stem Rot Resistance in Soybean. Crop Science. vol. 29, pp. 672–674, 1989.

*Primary Examiner*—David T. Fox
*Assistant Examiner*—Melissa L. Kimball
*Attorney, Agent, or Firm*—Pioneer Hi-Bred International, Inc.

[57] ABSTRACT

A method for introgressing brown stem rot (BSR) resistance into elite soybean germplasm is disclosed. The method involves using a genetically mapped locus associated with BSR resistance for marker-assisted selection during introgression of BSR resistance into elite soybean germplasm. Also disclosed are a method for confirming selection for BSR resistance; a quantitative trait locus associated with BSR resistance; and soybean lines bred to be resistant to BSR infestation.

35 Claims, 1 Drawing Sheet

POSITIONAL CLONING OF BROWN STEM ROT RESISTANCE GENES IN SOYBEANS

CROSS REFERENCE TO RELATED APPLICATIONS

This application is a continuation-in-part of U.S. Ser. No. 08/534,091, filed Sep. 26, 1995, issued as U.S. Pat. No. 5,689,035 on Nov. 18, 1997.

FIELD OF THE INVENTION

The present invention relates to plant breeding and plant genetics. More specifically, the present invention relates to methods for using marker assisted selection in the breeding of soybeans that are resistant to brown stem rot, and to quantitative trait loci useful in such methods, as well as cloning of genes for brown stem rot resistance.

BACKGROUND

Soybeans are a major cash crop and investment commodity in Ncirth America and elsewhere. Soybean oil is one of the most widely used edible oils, arid soybeans are used throughout the world in both animal feed and in human food production.

Brown stem rot (BSR) is a fungal disease of soybean [*Glycine max* (L.) Merr.] caused by *Phialophora gregata* (Allington and Chamberlain) W. Gams (syn. *Cephalosporium gragatum* Allington and Chamberlain). BSR occurs in many of the soybean production areas of the north-central USA (Allington 1946), the southeastern USA (Phillips 1970; Ross and Smith 1963), and Canada; and has been reported in Egypt, Japan, Mexico, and Yugoslavia (Sinclair and Backman 1989). It has caused an estimated average loss per year of 553,333 metric tons (approximately $112 million) of soybean production during each of the years 1989 to 1991 in the north-central USA (Doupnik, Jr. 1993). The severity of infection of soybean by *P. gregata* depends on the level of pathogenicity and the population density of the pathogen, as well as temperature, soil fertility, and the maturity status of the soybean variety (Gray 1971 and 1985; Mengistu and Gau 1986; Waller et al., 1992; Weber et al. 1966).

The environmental factors affecting BSR infection of soybean can be difficult for breeders to uniformly control with certainty. Susceptible plants not showing symptoms for BSR may be mistakenly classified as resistant because the environmental conditions were not conducive to the development of the disease. Thus, using genetic markers that are linked to BSR resistance loci as a way to screen soybean populations and select for linked BSR resistance loci may be more reliable than scoring BSR symptoms in field screenings.

BSR resistance in the soybean plant-introductions 'PI 84.946-2' (Chamberlain and Bernard 1968), 'PI 437.833' (Hanson et al. 1988), and 'PI 437.970' (Willmot and Nickell 1989) is controlled by the dominant alleles $Rbs_1$, $Rbs_2$, and $Rbs_3$ respectively (Hanson et al. 1988; Willmot and Nickell 1989). Other plant introductions having BSR resistance have also been identified (Nelson et al. 1989) but their respective resistance loci have not been determined. Most commercially available BSR-resistant soybean lines inherited their resistance from PI 84.946-2 through several cycles of breeding. Segregation among $F_{2:3}$ families from the cross "Century" X PI 84.946-2 indicates that PI 84.946-2 has two unlinked BSR resistance loci (Sebastian and Nickell 1985). These two loci should be $Rbs_1$ and $Rbs_3$ because the BSR-resistant soybean lines 'L78-4094' and 'BSR101' have $Rbs_1$ and $Rbs_3$, respectively, and both lines are descendent from PI 84.946-2 as their only source of BSR resistance (Sebastian and Nickell 1985; Hanson et al. 1988; Tachibana et al. 1987; Eathington et al. 1995). $Rbs_3$ is now assigned to BSR101 because all $F_2$ plants and $F_{2:3}$ families from the cross PI 437.970 X BSR101 were resistant to BSR (Eathington et al. 1995), and without segregation, the resistance locus is the same for both PI 437.970 and BSR101.

Genetic markers can be used to indirectly select for agronomically favorable genes among segregating individuals in plant breeding populations. Marker-assisted selection (MAS) is particularly useful when the desired trait is largely affected by the environment, which, as noted, often cannot be adequately controlled to optimize the expression of the trait. The greater the effect of an environment on a trait and the less that environment can be controlled, the less will be that trait's heritability and concomitant predictability of phenotypes. Genetic markers have highly reproducible phenotypes because their environment can be well controlled in the laboratory, conveying to them a heritability and predictability approaching unity. If a polymorphic genetic marker occurs within a few centimorgans of a gene affecting a desired trait, recombination events between the marker and gene would occur rarely, providing the high heritability and low error rate needed for reliable indirect selections for the favorable gene and the trait it governs.

Marker-assisted selection for BSR resistance can only be accomplished after one or more markers are found that are genetically linked to one or more BSR-resistance loci. For this reason RFLP markers to a locus associated with BSR resistance in the soybean variety BSR101 were genetically mapped. Based on the literature already described, this mapped resistance locus should be $Rbs_3$. These markers, and other markers that may be found linked to these markers, provide a new and valuable tool to soybean breeders for selecting and developing future soybean cultivars having BSR resistance from $Rbs_3$.

SUMMARY OF THE INVENTION

Therefore, it is an object of the present invention to provide a method of introgressing BSR resistance into non-resistant soybean germplasm. A locus associated with BSR resistance in soybean lines known to be resistant to BSR is used in marker-assisted selection during introgression of BSR resistance into elite soybean germplasm. Examples of soybean lines possessing the $Rbs_3$ locus include BSR101, BSR201, Archer, Newton, DSR262, DSR290, PI 84.946-2, and PI 437.970. The method of the present invention is useful in selecting for BSR resistant lines for use in a breeding program which will produce new, agronomically useful BSR resistant lines.

The method of the present invention involves the use of nucleic acid markers genetically linked with $Rbs_3$. The markers are used to select for BSR resistant lines in populations segregating for $Rbs_3$. For example, the markers can be used in genetic mapping of genetic material of soybean lines to be used in and/or that have been developed in a breeding program, allowing for marker-assisted selection during introgression of BSR resistance into elite germplasm.

Any art-recognized genetic mapping techniques may be utilized in the practice of the method of the present invention. Preferred embodiments will utilize Restriction Fragment Length Polymorphism (RFLP) mapping, Random Amplified Polymorphic DNA (RAPD) mapping, SSR or microsatellite mapping, and the like, using nucleic acid markers recognized for or applicable to the particular method applied.

It is also an object of the present invention to provide a method of confirming selection for BSR resistance. This is accomplished by identifying products of a soybean breeding program having in their genetic material the locus associated with resistance to BSR.

The present invention also relates to a mapped resistance locus associated with BSR resistance. Specifically, the locus of the invention is the Rbs$_3$ locus, mapped (or identified, defined or isolated) using identified nucleic acid markers or other equivalent segregating markers genetically linked with Rbs$_3$ and associated with BSR resistance.

It is an additional object of the present invention to provide soybeans resistant to BSR bred according to the method of the invention, or developed through the identification of parental lines possessing the locus of the invention.

It is an additional further object of the present invention to provide a method for cloning, identifying and isolating genes located within QTL associated with BSR resistance by positional cloning. A soybean genomic library is prepared, and probes are used to hybridize and select for homologous large-insert soybean genomic clones from the genomic library. The large-insert clones are then used to create a contig of cloned DNA inserts, and the gene or genes within one or more clones residing in the contig are identified. Markers that map to BSR associated QTL are used as probes, or alternatively PCR primers designed from sequenced markers can be used in the practice of the method. Ultimately, such identified genes are isolated.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit of the invention will become apparent to those skilled in the art from the detailed description.

DETAILED DESCRIPTION OF THE INVENTION

Figure 1:
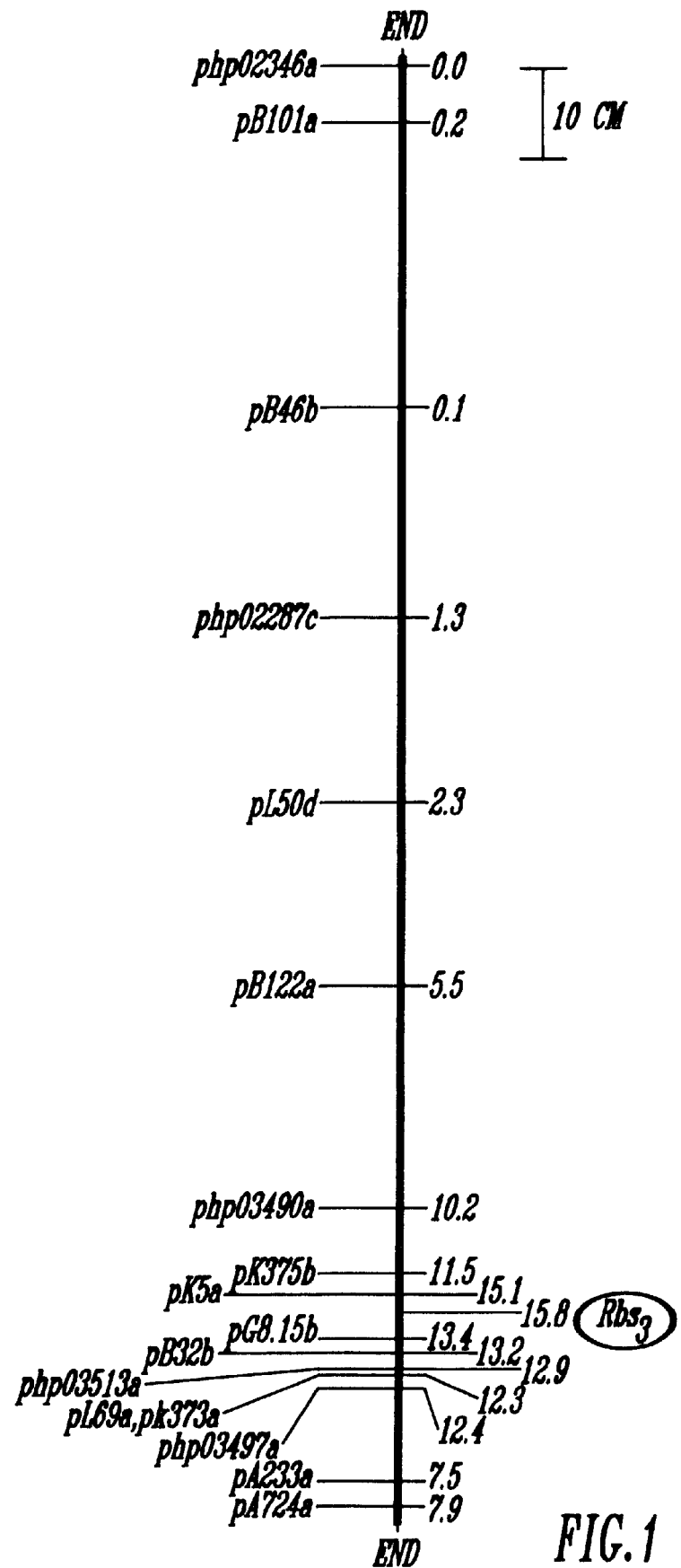
FIG. 1 shows locations of RFLP markers and Rbs$_3$, associated with brown stem rot resistance, on linkage-group J. Marker names are on the left and marker-QTL LOD scores are on the right of the group. LOD scores at markers were from single-locus analyses of additive gene effects using MAPMARKER/QTL. Genetic distances (cM) were from the recombinant-inbred function of MAPMARKER/EXP 3.0. A distance scale is shown. The longest line to the right of the linkage group shows the estimated position of Rbs$_3$ based on 2-cM interval mapping using MAPMARKER/QTL.

The present invention provides a novel and useful method for introgi-essing, in a reliable and predictable manner, BSR resistance into non-resistant soybean germplasm. The method involves the genetic mapping of a locus associated with BSR resistance. BSR resistance can be confirmed in any acceptable manner. For example, confirmation can be carried out in field tests, preferably in a field or fields in which BSR has been problematic.

The soybean line selected for mapping is subjected to DNA extraction. In a preferred embodiment the CTAB method (Murray and Thompson, Nucl. Acids Rev. 8:43214325, 1980; Keim et al., Soybean Gent. Newsl. 15:15–152, 1988) is used. Nucleic acid probes are used as markers in mapping the resistance loci, and appropriate probes are selected based upon the mapping method to be used. The probes can be either RNA or DNA probes, and mapping is performed using RFLP, RAPD, or microsatellite technology.

In a particular embodiment, DNA probes are used for RFLP markers. Such probes can come from, for example, Pst I-cloned genomic libraries, and the cloned inserts used as probes may be amplified, for example by PCR, LCR, NASBA™, or other amplification methods recognized in the art. For example, the markers useful in a preferred embodiment of the invention include the following: pB122a, php03490a, pK375b, pK5a, pG8.15b, pB32b, php03513a, pL69a, pK373a, php03497a, pA233a, or pA724a. Of course it will be apparent to those skilled in the art that other markers which map to the BSR resistance locus may be utilized in the practice of the invention. For RFLP mapping, restriction fragments are generated using specific restriction enzymes, and the digestion, electrophoresis, Southern transfers and nucleic acid hybridizations are conducted according to art-recognized techniques. See e.g., Keim et al., Theor. Appl. Genet. 77:786–792, 1989.

In alternative embodiments of the method of the invention, RAPD technology, AFLP technology, or SSR/microsatellite technology can be utilized for genetic mapping. A DNA preparation is amplified using art-recognized amplification techniques, and suitable nucleic acid markers are used.

In a soybean breeding program, the method of the present invention envisions the use of marker-associated selection for one or more loci at any stage of population development in a two-parent population, multiple parent population, or a backcross population. Such populations are described in Fehr, W. R. 1987, *Breeding Methods for Cultivar Development*, in J. R. Wilcox (ed.) *Soybeans: Improvement, Production, and Uses*, 2d ed.

Marker-assisted selection according to art-recognized methods may be made, for example, step-wise, whereby the BSR resistance locus is selected in more than one generation; or, as an alternative example, simultaneously, whereby the locus is selected in a single generation. Marker-assisted selection for BSR resistance may be done before, in conjunction with, or after testing and selection for other traits such as seed yield.

The DNA from target populations may be obtained from any plant part, and each DNA sample may represent the genotype of single or multiple plant individuals (including seed).

Marker-assisted selection may also be used to confirm previous selection for BSR resistance or susceptibility made by challenging plants with *P. gregata* in the field or greenhouse and scoring the resulting phenotypes.

The following examples are offered by way of illustration and not by way of limitation.

EXAMPLE 1

Genetic Mapping of the Rbs$_3$ Locus

Materials and Methods

Germplasm Development and Characteristics

A population of 328 recombinant-inbred lines (RILs) was licensed by Pioneer Hi-Bred International, Inc., from the Iowa State University. This population originated from a cross between two soybean max lines, 'Pi 437.654' and BSR101, and was developed by single-seed-descent inbreeding from the F$_2$ to the F$_{6:7}$ generation. It has been used in several previous genetic studies (Baltazar and Mansur 1992; Keim et al. 1994; Webb et al. 1995). PI 437.654 is a Maturity Group III plant introduction from China in the USDA soybean germplasm collection received from the USSR in 1980 (Nelson et al. 1988). It is susceptible to *P. gregata* (Waller et al. 1992). BSR101 is a Maturity Group I soybean variety developed at Iowa State University, and has a resistance to *P. gregata* that is derived from PI 84946-2 (Tachibana et al. 1987).

Brown Stem Rot Screening

A 266 line subset of the population was grown in 1992 on the southeast corner of the 'Bauer' field at the Pioneer soybean breeding station near St. Joseph, Ill., USA, and evaluated for reaction to *P. gregata*. Brown stem rot in soybeans had occurred previously in this field. The plot design was two replications of hill plots in random complete blocks. Hills were centered 100 cm apart within rows, and rows were 76 cm apart. Solid rows of the soybean variety P9202 were alternated between hill rows to reduce border effects due to plot-to-plot competition. P9202 is an erect, early maturing, BSR susceptible variety. Each hill plot consisted of 10 sample seeds and approximately 30 seeds of sorghum [*Sorghum bicolor* (L.)] killed, sterilized, and coated with hyphae of *P. gregata*. The hyphal mixture was equal proportions of four, *P. gregata* isolates originally taken from infected soybean plants in Illinois.

The plants in each hill plot were visually scored for the presence or absence of leaf browning, a characteristic of necrosis from BSR infection (Sinclair and Backman 1989), on 25 Aug., 9 Sept., and 11 Sept. 1992. The plots were viewed ion multiple dates to not miss symptoms on early maturing lines and symptoms appearing later on late maturing lines. Plots that had leaf browning characteristic of BSR on a3t least one scoring date were recorded susceptible, and plots that had no leaf symptoms on all scoring dates were recorded resistant.

Laboratory Methods

The following description of DNA extractions, RFLP procedures, and RFLP markers used in this study has been previously reported (Webb et al. 1995). DNA of soybean material was extracted using a CTAB method (Murray and Thompson 1980; Keim et al. 1988), with the following modifications. Lyophilized tissue was powdered by adding 2.5 g of glass beads (Fisher cat. #11-312A) and 750 mg of tissue in a 50 tube and shaking in a paint-an shaker. The concentration of CTAB (hexadecyltrimethyl-ammonium bromide) in the extraction and precipitation buffers was reduced from 1% to 0.5%. After the DNA was precipitated with CTAB, the DNA pellet was dissolved in 2 mL 1 M NaCl with shaking at 60° C., 200 rpm, for 2–3 hr. The DNA was re-precipitated by adding 4.5 mL ice-cooled 95% EtOH. The spooled DNA was washed with mL of 65%, then 1 mL of 85% EtOH, to further remove salts. After the EtOH washes, the DNA was dissolved in 500–1000 $\mu$L TE (10,1), diluted to 500 ng $\mu L^{-1}$, and stored at 4° C. until used.

Most RFLP markers used were from PstI-cloned genomic libraries and were either public (Keim and Shoemaker 1988) or proprietary (prefixed php) to Pioneer Hi-Bred International, Inc. Some RFLP markers used were from USDA-ARS (Beltsville, Md.) cDNA clones (prefixed pBLT). The cloned inserts used as probes were amplified by the polymerase chain reaction. Oligonucleotides of the $T_3$ and $T_7$ promoter regions of the phagemid vector pBS$^{+/-}$ were used as amplification primers. The restriction enzymes EcoRI, HindIII, EcoRv, DraI, TaqI, and HaeIII were used to digest the parental and population DNA. Approximately 900 RFLP markers were used against PI 437.654 and BSR101 to identify and map 355 RFLP markers segregating in the RIL population. The DNA digestions, electrophoresis, Southern transfers, and DNA hybridizations were conducted as described previously (Keim et al. 1989).

Data Analyses

Genetic linkages and distances between markers were estimated by maximum likelihood analysis of segregating RFLP-marker patterns in the RIL population, using the computer program MAPMAKER/EXP 3.0 (Lincoln et al. 1993) and a mapping protocol similar to one described by Landry et al. (1991). Centimorgan distances reported in this manuscript were considered comparable to those that would be obtained using an $F_2$ population.

Although the phenotypes were scored as either susceptible or resistant, the data were analyzed as a quantitative trait in order to test means associated with marker classes. Susceptible and resistant scores for each replication of each line were converted to '1' and '9', respectively. If a line had different scores between the two replications, it was removed from the data set. This was done to minimize scoring error caused by the chance escape of susceptible plants from infection.

The genome was scanned for quantitative-trait loci (QTL) by calculating likelihood statistics (LOD scores) based on an additive genetic model at each marker locus using MAPMAKER/QTL (Lincoln and Lander 1990). Based upon Lander and Botstein's simulations (1989) and the genome size and density of marker, loci used in this experiment, it was decided prior to analyses that a LOD score of 3.0 was an appropriate threshold for declaring linkage of a marker with a QTL.

Interval mapping (Lander and Botstein 1986) with MAPMAKER/QTL to estimate the positions of QTL relative to their nearby markers was performed with maximum-likelihood tests at positions every 2 cM between adjacently linked markers. Because inbred populations show approximately twice the recombination found in their $F_2$ generation (Haldane and Waddington 1931), the 2 cM distances used in this interval mapping were considered to be equivalent to the 1 cM distances calculated for the map using the RIL function of MAPMAKER/EXP 3.0.

Results and Discussion

Phenotypic Variation

Of the 266 lines evaluated for BSR leaf symptoms, 88 lines were scored resistant in one replication and susceptible in the other replication. Because these lines were inbred six generations by single-seed descent, each line had an average 98.5% probability for being homogeneous for each genetic locus involved with BSR resistance. The disease symptoms within each line should have been uniform unless the environment varied between the replications. To assess the genetic component for BSR resistance with a minimum amount of human and environmentally caused error, these 88 lines were removed from the data set before conducting the QTL analyses.

The remaining 178 lines were scored alike in both replications for resistance or susceptibility based on leaf symptoms. Seventy-two lines were scored susceptible and 106 lines were scored resistant. If BSR resistance in BSR101 is a single gene trait, we would expect approximately 89 lines in each of the resistant and susceptible classes; however, the observed numbers in each class deviated significantly from the expected ($X^2$=6.49, P–0.02–0.01).

The preponderance of lines scored resistant may be explained in several ways. BSR resistance in BSR101 is controlled by one dominant allele, $Rbs_3$, at one locus, but may also involve a minor locus (Eathington et al. 1995). Evidence of a minor locus in BSR101 is inconclusive, but another locus may confer resistance in more lines than had Rbs$_3$ in this population. The excess of lines scored resistant may also result from some plots being erroneously scored resistant because their environment conditions were not conducive to BSR infection. This would more likely have occurred for the 88 lines that were scored susceptible and resistant in different replications than for those lines scored resistant in both replications, and removing these 88 lines from the data set may have removed more susceptible than resistant lines from the analyses.

Rbs$_3$ Maps to Linkage-Group J

Genetic markers on only one linkage group showed significant (LOD>3.0) association with a QTL for brown stem rot resistance. This linkage group was named 'J' because the markers pB101, pB46, pK375, pA233, and pA724 (FIG. 1) were also found on linkage-group J of the June 1994 USDA-ISU RFLP linkage imap (Randy Shoemaker, personal communication). Given that BSR101 has only one major locus, Rbs$_3$, for brown stem rot resistance (Eathington et al. 1995) and PI 437.654 has no BSR resistance (Waller et al. 1992), Rbs$_3$ was the BSR resistance locus mapped with markers on group J.

Marker-assisted Selection

These markers or other segregating markers genetically linked with Rbs$_3$ can be used in soybean breeding to select for BSR resistant lines in populations segregating for Rbs$_3$. The populations in which these markers will be effective will be those in which BSR resistance is derived from either the original plant introductions, PI 84.946-2 or PI 437.970, descendants of these sources, or any other soybean determined to have a BSR resistance allele at the Rbs$_3$ locus. Markers used for selection in this way no longer need to be identified specifically by direct mapping of Rbs$_3$ from segregating phenotypes. Now that Rbs$_3$ has been identified and defined with genetic markers on linkage-group J, other markers not identified in this study but found to be linked to the markers shown here (FIG. 1) can be used to select Rbs$_3$ in soybean breeding programs.

EXAMPLE 2

Positional Cloning

Markers linked to the mapped QTL for BSR resistance are used in positional cloning of genes that reside within the QTL. Positional cloning first involves creating a physical map of a contig (contiguous overlapping of cloned DNA inserts), in the genomic region encompassing one or more marker loci and the target gene. The target gene is then identified and isolated within one or more clones residing in the contig. Having a clone of a gene allows it to be used in genetic studies, transformation, and the development of novel phenotypes.

Mapped BSR markers, especially those most closely linked to the QTL and those that flank the resistance QTL on both sides are used to identify homologous clones from soybean genomic libraries, including, for example, soybean genomic libraries made in bacterial artificial chromosomes (BAC), yeast artificial chromosomes (YAV), or P1 bacteriophage. These types of vectors are preferred for positional cloning because they have the capacity to carry larger DNA inserts than possible with other vector technologies. These larger DNA inserts allow the researcher to move physically farther with each overlap of clones along the chromosome. At least two such libraries, on BAC (Marek and Shoemaker 1996) and one YAC (Zhu et al. 1996), have been constructed and are available for positional cloning efforts in soybean. Mapped BSR markers are used as DNA probes to hybridize and select homologous genomic clones from such libraries. Alternatively, the DNA of mapped marker clones are sequenced to design PCR primers that amplify and therefore identify homologous genomic clones from such libraries. Either method is used to identify large-insert soybean clones that is then used to start or finish a contig constructed in chromosome walking to clone a BSR resistance QTL.

As examples, the positional cloning strategy was successfully used to clone the cystic fibrosis gene in humans (Rommens et al. 1989), an omega-3 desaturase gene in Arabidopsis (Arondel et al. 1992), a protein kinase gene (Pto) conferring fungal resistance in tomato (Martin et al. 1993), and the isolation of a YAC clone containing the jointless gene that suppresses abscission of flowers and fruit in tomato (Zhang et al. 1994). For reviews on position cloning, see Wicking and Williamson (1991), Gibson and Sommerville (1993), and Parris and Nelson (1993).

Applicant has made a deposit with the American Type Culture Collection (ATCC), Manassas, Va. 20110 USA. Marker php03490 was deposited under ATCC Designation No. 98488. Marker php03513 was deposited under ATCC Designation No. 98489. Marker php03497 was deposited under ATCC Designation No. 98494. E. coli DH5α strains comprising the markers were deposited with the ATCC on Jul. 8, 1997. The strains were tested for viability on Jul. 11, 1997 and on that date were capable of reproduction. The deposits were made by Pioneer Hi-Bred International, Inc., 700 Capital Square, 400 Locust Street, Des Moines, Iowa 50309-2340 and were in its posession since before the filing date of the application. Each of these deposits will be maintained in the ATCC depository, which is a public depository, for a period of 30 years, or 5 years after the most recent request, or for the effective life of the patent, whichever is longer, and will be replaced if any one of the deposits becomes nonviable during that period. Applicant imposes no restrictions on the availability of the deposited material from the ATCC; however, Applicant has no authority to waive any restrictions imposed by law on the transfer of biological material or its transportation in commerce.

All references cited herein are hereby expressly incorporated herein by reference.

References

Allington, W. B. (1946) Brown stem rot of soybean caused by an unidentified fungus. *Phytopatholoay*, 36:394.

Arondel, V., Lemieux, B., Hwant, I., Gibson, S., Goodman, H. M., Sommerville, C. R. (1992) Maped-based cloning of a gene controlling omega-3 fatty acid desaturation in Arabidopsis. *Science* 258:1353–1355.

Baltazar, B. M., Mansur, L. (1992) Identification of restriction fragment length polymorphisms (RFLP's) to map soybean cyst nematode resistance genes sin soybean. *Soybean Genet. Nwslett.*, 19:120–122.

Chamberlain, D. W., Bernard, R. L. (1968) Resistance to brown stem rot in soybeans. *Crop Sci.*, 8:728–729.

Doupnik, Jr. B. (1993) Soybean production and disease loss estimates for North Central United States from 1989 to 1991. *Plant Dis.*, 77:1170–1171.

Earthington, S. R., Nickell, C. D., Gray, L. E., (1995) Inheritance of brown stem rot resistance in soybean cultivar BSR 101. *J. Hered*, 86:55–60.

Gibson, S., Somerville, C. (1993) Isolating plant genes. *Trends Biotech* 11 (7):306–313.

Gray, L. E. (1971) Variation in pathogenicity of *Cephalosporum gregatum* isolates. *Phytopatholopy*, 61:1410–1411.

Gray, L. E. (1985) Brown stem rot of soybeans. *World Soy. Res. Conf. III*, Westview Press, Boulder, Colo. USA.

Haldane, J. B. S., Waddington, C. H. (1931) Inbreeding and linkage. *Genetics*, 16:357–374.

Hanson, P. M., Nickell, C. D., Gray, L. E., Sebastian, S. A. (1988) Identification of two dominant genes conditioning brown stem rot resistance in soybean. *Crop Sci.*, 28:41–43.

Keim P., Beavis, W. D., Schupp, J. M., Baltazar, B. M., Mansur, L., Freestone, R. E., Vahedian, M., Webb, D. M. (1994) RFLP analysis of soybean breeding populations: I. Genetic structure differences due to inbreeding methods. *Crop. Sci.*, 34:55–61.

Lander, E. S., Botstein, D. (1986) Strategies for studying heterogeneous genetic traits in humans by using a linkage map of restriction fragment length polyimorphisms. *Proc. Nat'l. Acad. Sci. USA*, 83:7353–7357.

Lander, E. S., Botstein, D. (1989) Mapping mendelian factors underlying quantitative traits using RFLP linkage maps. *Genetics*, 121:185–199.

Landry, B. S., Hubert, N., Etoh T., Harada, J. J., Lincoln, S. E. (1991) A genetic map for *Brassica napus* based on restriction fragment length polymorphisms detected with expressed DNA sequences. *Genome*, 34:543–552.

Lincoln, S. E., Daly, M. J., Lander, E. S. (1993) MAPMAKER/EXP. Whitehead Institute of Biomedical Research, Cambridge, Mass.

Lincoln, S. E., Lander, E. S. (1990) MAPMAKER/QTL. Whitehead Institute of Biomedical Research, Cambridge, Mass.

Marek, L. F., Shoemaker, R. C. (1996) Construction and size characterization of a bacterial artificial chromosome (BAC) library from soybean. Soybean Genet Newslett 23:126–129.

Martin, G. B., Brommonschenkel, S. H., Chunwongse, J., Fraary, A., Ganal, M. W., Spivey, R., Wu, T., Earle, E. D., Tanksley, S. D. (1993) Map based cloning of a protein kinase gene conferring disease resistance in tomato. Science 262:1432–1436.

Mengistu, A., Grau, C. R. (1986) Variation in morphological, cultural, and pathological characteristics of *Phialophora gregata* and Acremonium sp. recovered from soybean in Wisconsin. *Plant Dis.*, 70:1005–1009.

Nelson, R. L., Amdor, P. J., Orf, J. H., Cavins, J. F. (1988) Evaluation of the USDA soybean germplasm collection: maturity groups 000 to IV (PI 427.136 to PI 445.845). USDA-ARS Tech Bull 1726.

Nelson, R. L., Nickell, C. D., Orf, J. H., Tachibana, H., Gritton, E. T., Grau, C. R., Kennedy, B. W. (1989) Evaluating soybean germplasm for brown stem rot resistance. *Plant Dis.* 73:110–114.

Phillips, D. V. (1970) Incidence of brown stem rot of soybean in Georgia. *Plant Dis. Reg.*, 54:987–988.

Rommens, J. M., lannuzzi, M. C., Kerem, B-S., Drumm, M. L., Melnier, G., Dean, M., Rozmahel, R., Cole, J. L., Kennedy, D., Hidaka, N., Zsiga, M., 13uchwald, M., Riordan, J. R., Tsui, L-C., Collins, F. S. (1989) Identification of the cystic fibrosis gene: chromosome walking and jumping. Science 245:1059–1065.

Ross, J. P., Smith, T. J. (1963) Brown stem rot of soybean in North Carolina and Virginia. *Plant Dis. Rep.*, 47:329.

Sebastian, R. W., Nickell, C. D. (1985) Inheritance of brown stem rct resistance in soybeans. *J. Hered*, 76:194–198.

Sinclair, J. B., Backman, P. A. (1989) Compendium of soybean diseases. APS Press, St. Paul, Minn. USA.

Tachibana, H., Voss, B. K., Fehr, W. R. (1987) Registration of 'BSR101' soybean. *Crop Sci.*, 27:612.

Waller, R. S., Nickell, C. D., Gray, L. E. (1992) Environmental effects on the development of brown stem rot in soybean. *Plant Dis.*, 76:454–457.

Webb, D. M., Baltazar, B. M., Rao-Arelli, A. P., Schupp, J., Clayton, K., Keim, P., Beavis, W. D. (1995) Genetic mapping of soybean cyst nematode race-3 resistance loci in the soybean PI 437.654. *Theor. Apr. Genet.* (in press).

Weber, C. R., Dunleavy, J. M., Fehr, W. R. (1966) Influence of brown stem rot on agronomic performance of soybeans. *Aaron. J.*, 58:519–520.

Wicking, C., Williamson, B. (1991) From linked marker to gene. Trends Genet 7(9):288–293.

Willmot, D. B., Nickell, C. D. (1989) Genetic analysis of brown stem rot resistance in soybean. *Crop Sci.*, 29:672–674.

Zhang, H-B., Martin, G. B., Tanksley, S. D., Wing, R. A. (1994) Map-based cloning in crop plants: tomato as a model system II. Isolation and characterization of a set of overlapping yeast artificial chromosomes encompassing the jointless locus. Mol Gen Genet 244:613–621.

Zhu, T., Shi, L. Funke R. P., Gresshoff, P. M., Keim, P. (1996) Characterization and application of soybean YACs to molecular cytogenetics. Mol Gen Genet 252:483–488.

What is claimed is:

1. A method of selecting a first plant by marker assisted selection of a quantitative trait locus (QTL) associated with brown stem rot resistance, the method comprising the steps of:

(i) detecting a first nucleic acid from the first plant which is genetically linked to a locus corresponding to a marker selected from the group consisting of php0349a (ATCC Deposit No. 98488), php03513a Deposit No. 98489), and php03497a (ATCC Deposoit No. 98494); and, (ii) selecting the first plant comprising the first nucleic acid, thereby selecting the QTL.

2. The method of claim 1 wherein the nucleic acid maps within ten centimorgans of the selected locus.

3. The method of claim 1, wherein the locus corresponds to a marker which maps within linkage group J.

4. The method of claim 1, further comprising detecting a second nucleic acid from the first plant which is genetically linked to a locus corresponding to a marker selected from the group consisting of php0349a (ATCC Deposit No. 98488), php03513a (ATCC Deposit No. 98489), and php03497a (ATCC Depoosit No. 98494).

5. The method of claim 1, further comprising detecting a second nucleic acid from the first plant which is genetically linked to a locus corresponding to a marker selected from the group consisting of php0349a (ATCC Deposit No. 98488), php03513a (ATCC Deposit No, 98489), and php03497a (ATCC Deposit No. 98494), wherein the first and second nucleic acids flank the QTL.

6. The method of claim 1, wherein the first nucleic acid is a genomic nucleic acid comprising at least one locus corresponding to a marker selected from the group consisting of php0349a (ATCC Deposit No. 98488), php03513a (ATCC Deposit No. 98489), and php03497a (ATCC Deposit No. 98494.

7. The method of claim 1, wherein the first nucleic acid is a genoric nucleic acid comprising two or more loci corresponding to two or more markers selected from the group consisting of php0349a (ATCC Deposit No. 98488), php03513a (ATCC Deposit No. 98489), and php03497a (ATCC Deposit No. 98494).

8. The method of claim 1, wherein the first plant is a progeny plant from a plant breeding cross between a non-resistant soybean plant which is not resistant to brown stem rot and a resistant soybean plant which is resistant to brown stem rot.

9. The method of claim 8, further comprising crossing the first plant with a second plant to obtain progeny, where the progeny of the first plant comprise the QTL for brown stem rot resistance.

10. The method of claim 1 wherein the step of detecting the first nucleic acid comprises RFLP, RAPD, AFLP, or microsatellite analysis.

11. The method of claim 1, wherein the step of detecting the first nucleic acid comprises hybridization of a second nucleic acid to the first nucleic acid.

12. The method of claim 1, wherein the QTL is derived from a second plant selected from the group consisting of plant lines P1437.970, BSR101, P184.946-2, BSR201, Archer, Newton, DSR262, DSR290, and a descendant thereof.

13. The method of claim 1, wherein the QTL is $Rbs_3$.

14. A method of identifying a quantitative trait locus (QTL) associated with brown stem rot resistance in a plant, the method comprising detecting a first locus genetically linked to the QTL, wherein the first locus corresponds to a marker selected from the group consisting of: php0349a (ATCC Deposit No. 98488), php03513a (ATCC Deposit No. 98489), and php03497a (ATCC Deposit No. 98494.

15. The method of claim 14, further comprising detecting a second locus genetically linked to the QTL, wherein the second locus corresponds to a marker selected from the group consisting of: php0349a (ATCC Deposit No. 98488), php03513a (ATCC Deposit No. 98489), and php03497a ATCC Deposit No. 98494).

16. The method of claim 14, further comprising detecting a second locus genetically linked to the QTL, wherein the second locus corresponds to a marker selected from the group consisting of: php0349a (ATCC Deposit No. 98488), php03513a (ATCC Deposit No. 98489), and php03497a (ATCC Deposit No. 98494).

17. The method of claim 14, wherein the locus corresponds to a marker which maps within linkage group J.

18. The method of claim 14, wherein the step of detecting the first locus comprises detecting a nucleic acid genetically linked to the first locus.

19. The method of claim 14, wherein the step of detecting the locus comprises detecting a nucleic acid genetically linked to the first locus, wherein said detection is performed by RFLP, RAPD, AFLP, or microsatellite analysis.

20. The method of claim 14, wherein the step of identifying the locus comprises hybridization of a nucleic acid probe to the locus.

21. A method of positional cloning of a nucleic acid, the method comprising the steps of:

(i) identifying a first nucleic acid genetically linked to a locus corresponding to a marker selected from the group consisting of: php0349a (ATCC Deposit No. 98488), php03513a (ATCC Deposit No. 98489), and php03497a (ATCC Deposit No. 98494); and (ii) cloning the first nucleic acid.

22. The method of claim 21, wherein the first nucleic acid is a quantitative trait locus (QTL) comprising $Rbs_3$.

23. The method of claim 21, further comprising hybridizing a second nucleic acid comprising the locus to a genomic library and selecting a clone that hybridizes to the second nucleic acid and comprises a second locus which confers brown stem rot resistance in a soybean plant.

24. The method of claim 21, further comprising hybridizing a second nucleic acid comprising the locus to a genomic library and selecting a clone that hybridizes to the second nucleic acid, wherein the genomic library is selected from the group consisting of a BAC soybean genomic library, a YAC soybean genomic library, and a P1 bacteriophage soybean genomic library.

25. The method of claim 21, further comprising identifying overlapping clones.

26. The method of claim 21, wherein the first nucleic acid maps between two markers selected from the group consisting of: php0349a (ATCC Deposit No. 98488), php03513a (ATCC Deposit No. 98489), and php03497a (ATCC Deposit No. 98494).

27. The method of claim 21, wherein the first nucleic acid is amplified by PCR prior to cloning of the first nucleic acid.

28. The method of claim 21, wherein the first nucleic acid is proximal to the selected locus.

29. The method of claim 21, further comprising the step of identifying a coding region encoded by the first nucleic acid.

30. The method of claim 29, wherein the coding region maps to a quantitative trait locus (QTL) comprising $Rbs_3$.

31. The method of claim 29, wherein the first nucleic acid maps within ten centimorgans of the selected locus.

32. An isolated quantitative trait locus (QTL) associated with brown stem rot resistance in a soybean plant, wherein the QTL is proximal to a locus corresponding to a marker selected from the group consisting of: php0349a (ATCC Deposit No. 98488), php03513a (ATCC Deposit No. 98489), and php03497a (ATCC Deposit No. 98494).

33. The isolated OTL of claim 32, wherein the QTL is $Rbs_3$.

34. A transgenic plant comprising an isolated quantitative trait locus (QTL) associated with brown stem rot resistance in a plant, and wherein the OTL is genetically linked to a marker selected from the group consisting of: php0349a (ATCC Deposit No. 98488), php03513a (ATCC Deposit No. 98489), and php03497a (ATCC Deposit No. 98494).

35. The transgenic plant of claim 34, wherein the QTL is $Rbs_3$.

* * * * *